United States Patent
Pigamo

(10) Patent No.: US 8,889,925 B2
(45) Date of Patent: Nov. 18, 2014

(54) PROCESS OF FLUORINATION IN LIQUID PHASE

(75) Inventor: Anne Pigamo, Francheville (FR)

(73) Assignee: Arkema France, Colombes (FR)

(*) Notice: Subject to any disclaimer, the term of this patent is extended or adjusted under 35 U.S.C. 154(b) by 33 days.

(21) Appl. No.: 13/583,293

(22) PCT Filed: Mar. 10, 2010

(86) PCT No.: PCT/IB2010/001114
§ 371 (c)(1),
(2), (4) Date: Sep. 7, 2012

(87) PCT Pub. No.: WO2011/110889
PCT Pub. Date: Sep. 15, 2011

(65) Prior Publication Data
US 2013/0041191 A1    Feb. 14, 2013

(51) Int. Cl.
*C07C 17/20* (2006.01)
*C07C 21/18* (2006.01)
*C07C 21/04* (2006.01)
*C01B 7/07* (2006.01)

(52) U.S. Cl.
CPC .............. *C07C 17/206* (2013.01); *C07C 21/18* (2013.01); *C07C 21/04* (2013.01); *C01B 7/0712* (2013.01)
USPC ........... 570/160; 570/164; 570/165; 570/166; 570/167; 570/168; 570/135

(58) Field of Classification Search
USPC ................................................. 570/160, 156
See application file for complete search history.

(56) References Cited

U.S. PATENT DOCUMENTS

| 2,787,646 | A | | 4/1957 | Haszeldine | |
| 4,091,043 | A | * | 5/1978 | Ohsaka et al. | 570/170 |
| 4,885,416 | A | * | 12/1989 | Mader | 570/170 |
| 5,684,219 | A | | 11/1997 | Boyce et al. | |
| 5,714,754 | A | * | 2/1998 | Nicholas | 250/221 |
| 5,969,198 | A | | 10/1999 | Thenappan et al. | |
| 7,009,083 | B2 | * | 3/2006 | Pennetreau et al. | 570/168 |
| 8,071,825 | B2 | | 12/2011 | Johnson et al. | |
| 2004/0186323 | A1 | * | 9/2004 | Banister et al. | 568/451 |
| 2009/0030247 | A1 | | 1/2009 | Johnson et al. | |
| 2009/0203945 | A1 | | 8/2009 | Mukhopadhyay et al. | |
| 2010/0036179 | A1 | | 2/2010 | Merkel et al. | |
| 2010/0191025 | A1 | * | 7/2010 | Perdrieux | 570/155 |
| 2012/0053371 | A1 | | 3/2012 | Johnson et al. | |

FOREIGN PATENT DOCUMENTS

| EP | 2 151 425 A2 | 2/2010 |
| WO | WO 2009/018561 A2 | 2/2009 |
| WO | WO 2009/026526 A1 | 2/2009 |
| WO | WO 2009018561 A2 * | 2/2009 |

OTHER PUBLICATIONS

International Search Report of PCT/IB2010/001114 (Nov. 8, 2010).

* cited by examiner

*Primary Examiner* — Jafar Parsa
*Assistant Examiner* — Medhanit Bahta
(74) *Attorney, Agent, or Firm* — Millen, White, Zelano & Branigan, P.C.

(57) ABSTRACT

The present invention provides a process of fluorination in liquid phase in a solvent medium of a compound of formula (II) $CX_1X_2=CZCX_3X_4X_5$, in which Z represents H, Cl or F, and each $X_1$ represents independently hydrogen or chlorine, given that at least one of the $X_1$ represents a chlorine.

15 Claims, 2 Drawing Sheets

PROCESS OF FLUORINATION IN LIQUID PHASE

FIELD OF THE INVENTION

The aim of the invention is the fluorination in liquid phase of chlorinated derivatives of propene, and in particular fluorination in liquid phase of 1,1,2,3-tetrachloropropene (HFO 1230xa) in 2-chloro-3,3,3-trifluoropropene (HFO 1233xf).

TECHNICAL BACKGROUND

The protocol of Montreal for the protection of the ozone layer led to the end of the use of chlorofluorocarbons (CFCs). Less aggressive compounds for the ozone layer, such as the hydrofluorocarbons (HFCs) e.g. HFC-134a replaced chlorofluorocarbons. These latter compounds were indeed shown to provide greenhouse gases. There exists a need for the development of technologies which present a low ODP (ozone depletion potential) and a low GWP (global warming potential). Although the hydrofluorocarbons (HFCs), which are compounds which do not affect the ozone layer, were identified as interesting candidates, they exhibit a relatively high GWP value. There still exists the need to find compounds which exhibit a low GWP value. Hydrofluoroolefins (HFO) were identified as being possible alternatives with very low ODP and GWP values.

Several processes of production HFOs compounds, in particular of propenes, were developed.

WO2009/018561 describes the fluorination of 1230xa in continuous liquid phase in the presence of a catalyst in particular $SbCl_5$. The desired product is the 244bb, that is the saturated product, the product 1233xf representing only a low fraction. The conditions of selected reactions are such that the medium of reaction is either only the catalyst or a catalyseur/1230xa mixture.

US2009/0099396 describes the fluorination of 1230xa in 245eb in liquid phase, in a medium made up of catalyst, again $SbCl_5$.

WO2007/079431 describes fluorination in liquid phase starting from the 1233xf, to prepare 244bb, which is a saturated compound.

WO2008/149011 describes fluorination in liquid phase in the presence of an ionic liquid of a propene. It is indicated generally that 1233xf and/or 1234yf (2,3,3,3-tetrafluoropropene) can be obtained by conversion of 1230xa.

WO2009/003084 describes fluorination in liquid phase in the absence of catalyst of 1230xa in 1233xf.

In the above patents, it is in general the gaseous phase which is analyzed. There is no evaluation of the rate of retention of the reactants in liquid phase whereas the organic liquid phase constitutes a large part of the material balance. However, phenomena of polymerization were observed in the liquid phase generating an important loss of output.

One thus seeks to limit the polymerization of the starting products, while preserving a high output of reaction. The limitation of the polymer formation will allow a continuous operation, without the risk of clogging the reaction zones and the feed ducts or the withdrawal pipes of reactants or products.

SUMMARY OF THE INVENTION

The invention thus provides a process of fluorination in liquid phase in a solvent medium of a compound of formula II $CX_1X_2=CZCX_3X_4X_5$, in which Z represents H, Cl or F, and each $X_i$ represents independently hydrogen or chlorine, given that at least one of the $X_i$ represents a chlorine.

According to one embodiment in formula II, groups $X_i$ represent hydrogen or chlorine, with a number of chlorine atoms from 1 to 3; and/or Z is H or Cl. Preferably in formula II, $X_1$ and $X_2$ represent each one atom of chlorine and at least one of $X_3$, $X_4$ and $X_5$ represents a chlorine atom.

According to one embodiment, the product of fluorination is a compound of formula I $CF_3CZ=CX_4X_5$, in which Z, $X_4$ and $X_5$ have the previous significances.

The invention is especially suited for the following reactions:
(i) fluorination of 1,1,2,3-tetrachloropropene into 2-chloro-3,3,3-trifluoropropene;
(ii) fluorination of 1,1,3,3-tetrachloropropene into 1-chloro-3,3,3-trifluoropropene;
(iii) fluorination of 1,1,3-trichloro,2-fluoropropene into 2,3,3,3-tetrafluoropropene.

According to one embodiment, the product of the solvent is selected from 1,2-dichloroethane, 1,2,3-trichloropropane, 1-chloro-1-fluoroethane, 1,1-difluoroethane, 1,1-dichloroethane and 1,3-dichloro-1-fluorobutane, 1,1,1,3,3-pentafluorobutane and 1,1,2-trichloro-2,2-difluoroethane, or a mixture thereof, advantageously 1,1,2-trichloro-2,2-difluoroethane. The solvent can be present in a quantity for a dilution ratio from at least 20%, preferably between 20 and 80%, advantageously between 40% and 60%.

According to one embodiment, a catalyst is used, preferably an ionic liquid. The molar ratio catalyst/solvent can be comprised between 10 mol % and 50 mol %, preferably between 15 mol % and 30 mol %.

According to one embodiment, chlorine is added during the reaction, preferably according to a molar ratio from 0.05 to 15 mole %, preferably 0.5 to 10 mole % of chlorine per mole of starting compound.

According to one embodiment, the reaction is withdrawn in the gaseous state.

According to one embodiment, a gas is injected, preferably anhydrous HCl. The flow of gas, compared to the flow of the starting product can be between 0.5:1 and 5:1, advantageously, between 1:1 and 3:1.

The invention also provides a process comprising:
(i) contacting 1,1,2,3-tetrachloropropene with hydrogen fluoride in a liquid phase in a solvent under conditions sufficient to form a reaction mixture comprising 2-chloro-3,3,3-trifluoropropene;
(ii) separating the reaction mixture into a first stream comprising HCl, and a second stream comprising HF, 2-chloro-3,3,3-trifluoropropene and 1,1,1,2-tetrafluoro-2-chloropropane.

According to one embodiment, the reaction mixture obtained at step (i) comprises, as a molar composition, HCl between 20 and 60%, HF between 10 and 40%, 2-chloro-3,3,3-trifluoropropene between 5 and 20%, 1,1,1,2-tetrafluoro-2-chloropropane between 0.5 and 5%, 2,3-dichloro-3,3-difluoropropene below 2% and solvent below 2%.

According to one embodiment, step (ii) is a distillation step.

According to one embodiment, the second stream is further separated, preferably by decantation, into a HF stream containing mainly HF, preferably with a content between 75 and 99%, and an organic stream containing 2-chloro-3,3,3-trifluoropropene and 1,1,1,2-tetrafluoro-2-chloropropane. The organic stream is further purified or is sent to a further process step for further conversion, preferably into 2,3,3,3-tetrafluoropropene.

According to one embodiment, the process further comprises a purging step for withdrawing heavies formed during step (i).

The invention also provides a process for preparing 2,3,3,3-tetrafluoropropene, comprising the following steps:
(i) preparation of the fluorination of 1,1,2,3-tetrachloropropene into 2-chloro-3,3,3-trifluoropropene according to the invention as defined herein;
(ii) conversion of 2-chloro-3,3,3-trifluoropropene into 2,3,3,3-tetrafluoropropene.

According to one embodiment, the conversion of stage (ii) is a catalytic gas phase conversion.

The invention also provides a composition comprising, expressed as molar concentration, HCl between 20 and 60%, HF between 10 and 40%, 2-chloro-3,3,3-trifluoropropene between 5 and 20%, 1,1,1,2-tetrafluoro-2-chloropropane between 0.5 and 5%, 2,3-dichloro-3,3-difluoropropene below 2% and solvent below 2%.

DETAILED DESCRIPTION OF EMBODIMENTS

Figure 1:
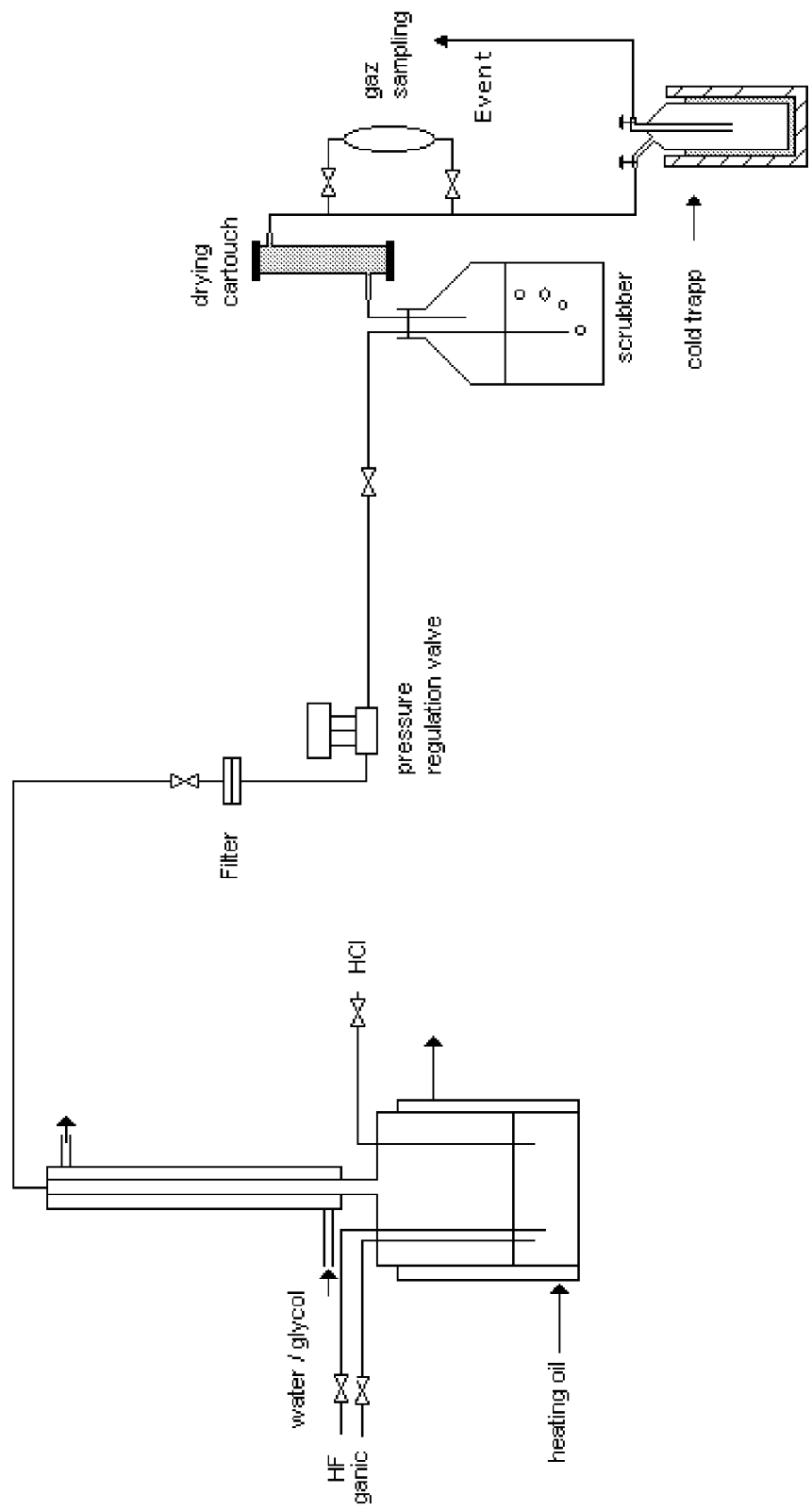
FIG. 1 is a representation of the experimental device used in the examples.

The invention is based on the use of a solvent phase, which makes it possible to avoid the reactions of polymerization (in acidic medium) and formation of the heavies. To maintain the output, it is not necessary to use large amounts of catalyst. The starting compound is a propene substituted by at least one chlorine atom, preferably at least 3 chlorine atoms and advantageously 4 chlorine atoms.

The starting compound has as a formula II

$$CX_1X_2=CZCX_3X_4X_5 \quad (II)$$

with Z which represents H, Cl or F, and the $X_i$ which represent independently hydrogen, chlorine, given that at least one of the $X_i$ represents a chlorine. Advantageously, the $X_i$ represents hydrogen or chlorine, with a number of chlorine atoms from 1 to 3.

Advantageously, Z is H or Cl.

According to an embodiment, $X_1$ and $X_2$ each represent one chlorine atom and at least one of $X_3$, $X_4$ and $X_5$ represents a chlorine atom.

Advantageously the fluorinated product may, according to an embodiment, be represented by formula I:

$$CF_3CZ=CX_4X_5 \quad (I)$$

in which Z, $X_4$ and $X_5$ have the previous significances.

According to an embodiment, the starting compound is the 1230xa (1,1,2,3-tetrachloropropene) and the final product is the 1233xf (2-chloro-3,3,3-trifluoropropene).

According to another embodiment, the starting compound is the 1230za (1,1,3,3-tetrachloropropene) and the final product is the 1233zd (1-chloro-3,3,3-trifluoropropene).

According to an embodiment, the starting compound is the 1240zf (3,3,3-trichloropropene, $CCl_3$—CH=$CH_2$) and the final product is the 1243zf (3,3,3-trifluoropropene).

According to an embodiment, the starting compound is the 1240za (1,1,3-trichloropropene, $CCl_2$=CH—$CH_2Cl$) and the final product is the 1243zf (3,3,3-trifluoropropene).

The reaction is implemented in a liquid solvent medium, the reaction zone being either charged at the beginning with the necessary quantity of solvent, or fed continuously with this quantity of solvent (possibly preliminary mixed with the raw material). The first alternative is preferred, injections with a view of adjusting the quantity of solvent may however be carried out if necessary.

The reaction temperature is such that the reactants are liquid. According to an embodiment the reactants are liquid while the reaction product is gaseous (in particular at room temperature, 20° C.). The fact that the reaction products are gaseous allows their recovery in a gaseous phase at the exit of the reaction zone. For example, the reaction may be implemented at a temperature ranging between 10° C. and 200° C., preferably between 20° C. and 150° C., advantageously between 50 and 140° C.

According to the invention, this stage is in particular implemented under a pressure higher than 2 bar. Advantageously, the pressure lies between 4 and 50 bars, in particular between 5 and 10 bars.

The molar ratio HF: starting compound lies generally between 3:1 and 50:1, preferably between 5:1 with 10:1.

The average dwell time in the reaction zone may be in the range between 1 and 50, preferably between 6 and 20 hours.

The solvent used is an inert organic solvent under the reaction conditions. Such a solvent will be generally saturated, advantageously in C2 to C6, in order to avoid the reactions of addition. Such solvents can for example be those mentioned in patent application FR2733227. Such solvents have a boiling point (measured at atmospheric pressure), for example higher than 40° C., advantageously higher than 50° C., in particular higher than 60° C. Higher reaction temperatures will imply higher pressures, so that the boiling point under the conditions of reaction is higher than the temperature of implementation of the reaction.

One can in particular mention as a solvent the saturated compounds of ethane, propane or butane, substituted by at least two atoms of halogen, chosen among chlorine and fluorine, or a mixture thereof. As an example one can mention 1,2-dichloroethane, 1,2,3-trichloropropane, 1-chloro-1-fluoroethane, 1,1-difluoroethane, 1,1-dichloroethane and 1,3-dichloro-1-fluorobutane, 1,1,1,3,3-pentafluorobutane and 1,1,2-trichloro-2,2-difluoroethane, or a mixture thereof. A preferred solvent is the 1,1,2-trichloro-2,2-difluoroethane (F122). One can also use perchloroethylene. One can also use possibly reactive solvents, in so far as the product of their reaction is a nonreactive solvent. For example, one can also use the precursor of F122, namely F121 ($CCl_2F$—CHCl).

The quantity of solvent is such that a minimum dilution ratio is reached during the reaction. In particular, this dilution ratio is at least 20%, in particular between 20 and 80%, advantageously between 40% and 60%, the dilution ratio being defined as the ratio between the volume of solvent and the total liquid volume in the reaction zone.

The reaction may not be catalyzed but the presence of a catalyst is advantageous. The catalysts may be catalysts known by the person skilled in the art of fluorinations in liquid phase.

One can use an acid of Lewis, a catalyst containing a metal halide, in particular containing halide of antimony, tin, tantalum, titanium, metals of transition such as molybdenum, niobium, iron halides, cesium, oxides of metals of transition, halides of metals of the IVb group, halides of metals of the Vb group, a fluorinated chromium halide, a fluorinated chromium oxide or a mixture of both. One can advantageously use metal chlorides and fluorides. Examples of such catalysts include: $SbCl_5$, $SbCl_3$, $TiCl_4$, $SnCl_4$, $TaCl_5$, $NbCl_5$, $TiCl_4$, $FeCl_3$, $MoCl_6$, $CsCl$, and their corresponding fluorinated derivatives. Pentavalent metal halides are suitable.

Advantageously one will use a catalyst containing an ionic liquid. These ionic liquids are particularly interesting for fluorination by HF in liquid phase. One will be able to mention the ionic liquids described in patent applications WO2008/149011 (in particular from page 4, line 1 to page 6 line 15, included by reference) and WO01/81353 in the name of the applicant, as well as the reference "liquid-phase HF Fluorination", Multiphase Homogeneous Catalysis, Ed. Wiley-VCH, (2002), 535.

One can operate with variable ratios catalyst/solvent, but in general one will prefer that this molar ratio lies between 10 mol % and 50 mol %, preferably between 15 mol % and 30 mol %.

A chlorine stream may be used to increase the lifespan of the catalyst, typically in a quantity from 0.05 to 15 mole %, preferably 0.5 to 10 mole % of chlorine per mole of starting compound (here 1230xa). Chlorine may be introduced pure or mixed with an inert gas such as nitrogen. The use of an ionic catalyst allows using small quantities of chlorine.

A polymerization inhibitor may be used if need be; typically in a quantity of 50-1000 ppm, preferably 100-500 ppm. This polymerization inhibitor can be for example p-methoxyphenol, t-amylphenol, limonene, d,1-limonene, quinones, hydroquinones, epoxides, amines and their mixtures.

It is also possible that the product of the reaction be stripped using a light gas allowing its drive by stripping. Such a gas with its stripping effect also makes it possible to limit the quantity of unsaturated organics in the medium.

If it is preferred that the reaction product be gaseous, it is also possible as that it is rather in liquid form at the reaction pressure. The continuous extraction of the reaction product can become delicate; the use of a stripping light gas facilitates the extraction by mechanical entrainment (or formation of an azeotrope). The addition of a gaseous compound can be advantageous for the output of the reaction, which can be favoured for example by the improvement of agitation (bubbling). The addition of a gaseous compound also allows, in a surprising way, decreasing the formation of heavy compounds (polymers). Without wishing to be bound by a theory, the applicant belives that the gaseous compound enhances the displacement of the chemical reaction and possibly the formation of saturated compounds. This gas can be inert as the nitrogen or helium or the gas can be preferably HCl.

Advantageously, this added gas is anhydrous hydrochloric acid. The flow of the stripping gas is determined according to the operating conditions. For example, the flow of HCl, compared to the flow of starting product is such that the molar ratio HCl: starting product lies between 0.5:1 and 5:1, advantageously, between 1:1 and 3:1.

The fluorination process in liquid phase according to the invention can be implemented continuously or semi-continuously. According to the preferred embodiment, the process is continuous. HF can be introduced partly with the catalyst during the loading of the reaction zone.

The reactants (starting product and HF) and other compounds used in the reaction (chlorine, anhydrous HCl) can be fed in the reactor at the same place or at different places of the reactor. A preferred embodiment is when the gaseous compounds are injected in the bottom of the reactor, in particular in order to enhance the mechanical stripping.

If a recycling is used, one can recycle directly at the inlet of the reactor or on a feed duct.

The reaction is implemented in a reactor dedicated to the reactions involving halogens. Such reactors are known to the skilled worker and can comprise coatings containing Hastelloy®, Inconel®, Monel® or fluoropolymers. The reactor can be equipped with means for heat transfer.

The process according to the invention also makes it possible to prepare a starting compound in the synthesis of the 1234yf. There exists a second stage then.

The second stage of the method of preparation of the 1234yf is a reaction of fluorination of the 2-chloro-3,3,3-trifluoro-1-propene (1233xf) obtained at the previous stage in 2,3,3,3-tetrafluoro-1-propene, the desired product.

The two stages can be implemented continuously or in a discontinuous way, with intermediate storage of the 1233xf.

This second stage can comprise direct fluorination in the presence of HF, on a catalyst, in gas phase. The catalysts of fluorination likely to be used are for example oxyfluoride of chromium, fluoride and oxyfluoride of aluminum, supported catalyst containing a metal such as Cr, Zn, Ti, V, Zr, Mo, Ge, Sn, Pb, Ni. The temperatures, pressures and contact times are easily determined by the skilled worker.

Such a process is described, in reference to the 1233zd compound which leads to compound 1234ze, in patent application EP-A-1067106, (in particular example 1), to which it is made reference. The application of the process to the starting compound 1233xf will lead to the formation of the product 1234yf. The concomitant formation of the product of hydrofluorination is possible, although not desired. The saturated reaction product can then be dehydrohalogenated, under conditions similar to those of the second stage of this process, to lead to the desired product.

This second stage can also comprise two sub-stages, a first sub-stage of formation of the product 1,1,1,2-tetrafluoro-2-chloropropane (244bb), then one second sub-stage of dehydrochlorination of this product into the desired 1234yf.

The first sub-stage comprises the hydrofluorination of the 1233xf, which can be implemented under known conditions. For example, the reaction can be done in gas or liquid phase, on a catalyst which can be an acid of Lewis, or a halide of a metal, such as for example $SbCl_5$, $SbCl_3$, $SbF_5$, $SnCl_4$, $TiCl_4$, $FeCl_3$, etc. The temperature can be comprised between 50° C. and 400° C., for example from 150° C. to 300° C., in particular at a temperature which is not very different from that of the first stage. The contact time is determined according to desired conversion and selectivity. The first sub-stage is in particular described in document WO2007/079431, from page 8, line 17 to page 10, line 16 and examples 5A, 5B and 6, to which it is made reference. One may also refer to document WO2008/040969, pages 16 & 17. In this reaction, the ratio HF: 1233xf is preferably higher than 5:1, and in general ranging between 5:1 and 50:1, or between 15:1 and 30:1, in order to enhance the reaction of fluorination.

The second sub-stage is a stage of dehydrochlorination, which is implemented under the conditions described above for the reaction of dehydrochlorination of the second stage of the method of preparation of the 1234yf. For this second sub-stage one may refer to document WO2007/079431, page 10, line 18 to page 12, line 14 and example 6, to which it is made reference. One may also refer to document WO2008/040969, pages 16 & 17.

These sub-stages can still comprise a stage of formation of compound 245cb (1,1,1,2,2-pentafluoropropane) by addition of HF to the product 244bb, which can in turn lead to the 1234yf by dehydrofluorination.

Figure 2:
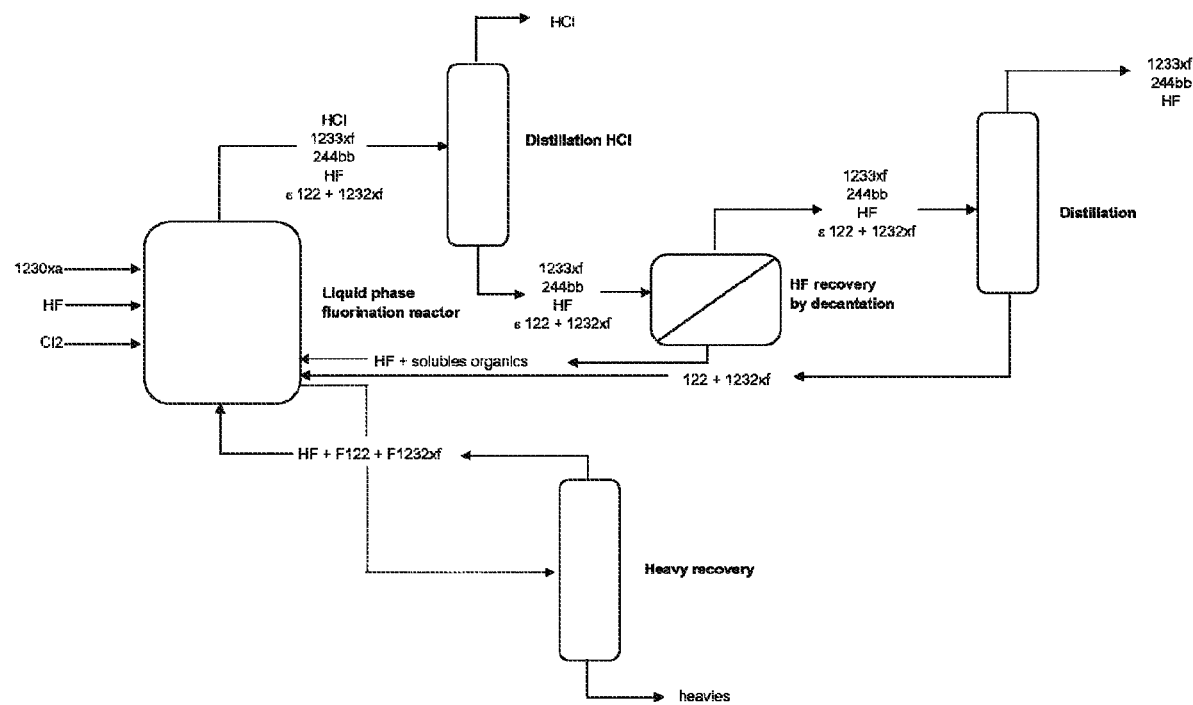
FIG. 2 is a schematic representation of a process implementing the invention.

FIG. 2 is a schematic representation of a process according to an embodiment of the invention. In FIG. 2, the solvent indicated is the 122 but another solvent can be used. In the same way, the process is described in relation to the starting product 1230, but another starting product can be used.

The reactor (equipped with a catalyst stripping column, not shown in the figure) for the liquid phase reaction is charged with solvent, then is supplied with 1230xa, and HF; a stream of $Cl_2$ is injected into the reaction zone. A stream of anhydrous HCl could also be injected. The stream which is withdrawn from the reaction zone is in a gaseous form and mainly comprises 1233xf, 244bb, HCl, HF as well as traces of stripped solvent 122 and 1232xf (2,3-dichloro-3,3-difluoropropene). The molar composition can typically be as follows: HCl between 20 and 60%, HF between 10 and 40%, the 1233xf between 5 and 20%, the 244bb between 0.5 and 5%, and solvent (here 122) below 2% (typically between 0.5 and 2%), the 1232xf below 2% (typically between 0.5 and 2%). This stream is introduced into a distillation column of HCl. At the top of the column is withdrawn a stream of HCl; at the bottom of the column a stream containing 1233xf, 244bb, HF as well as traces of 122 and 1232xf is withdrawn. This stream is sent towards a stage of separation by decantation. This decantation leads to two streams. The first stream comprises HF and soluble organics (1233xf, 244bb, 1232xf and 122, the HF content being between 75 and 99%) which is returned to the fluorination reaction. The second stream comprises 1233xf, 244bb, still a quantity of HF as well as traces of 122 and 1232xf. This stream is sent in a distillation column to be separated there. The traces of 122 and 1232xf are recovered at the bottom and are returned towards the fluorination reactor. The 1232xf will not build up, since it is an intermediate compound. A stream containing HF, 1233xf and 244bb is withdrawn at the top. This top stream can be further separated or can be sent directly towards the next step, which can be a catalytic gas phase fluorination reaction, where conversion into 1234yf takes place. At the bottom of the reactor a stream containing the heavies is withdrawn. It is believed, without wishing to be bound, that the heavies comprise oligomers of the $C_6F_6H_2Cl_2$ type. The bottom of the fluorination reactor is purged with a flow and a frequency such that the accumulation of heavies is avoided (rate of purging being defined by both a flow and frequency of purging as the skilled man can easily determine). This stream is treated in a column of recovery of the heavies. These heavies are eliminated at the bottom of this column. At the top of the column a stream containing HF, 122 and 1232xf is recovered; this stream is recycled towards the fluorination reactor.

EXAMPLES

The following examples illustrate the invention without limiting it.

Equipment used is described with reference to FIG. 1. It consists of an autoclave of a capacity of 1 liter with a dual envelope, made of stainless steel 316L, which is agitated using a magnetic stirrer. It is equipped with a measure of pressure and temperature. Apertures on the head of the autoclave allow the introduction of the reactants and degasification. It comprises at the top a condenser as well as a valve for regulating the pressure. The condenser is controlled in temperature using an independent thermostated bath. For all the tests, the temperature of the thermostated bath is set to 90° C.

The products of the reaction are extracted continuously during the reaction. They enter a water wash-bottle which collects hydracids HF and HCl and then are cold trapped in liquid nitrogen. The increase of weight of the wash-bottle and of the trap makes it possible to establish a material balance. The analysis is made then by gas phase chromatography on a sample of expanded liquid. The analysis by chromatography is carried out using a column CP Sil 8, dimensions 50 m*0.32 mm*5 µm. The programming of temperature of the furnace is the following one: 40° C. during 10 min then slope of 4° C./min until 200° C.

At the end of the period of reaction, the reaction medium is degassed so as to evacuate residual HF. For this period of degasification, the organics possibly drawn are also trapped, always after having crossed the wash-bottle which makes it possible to eliminate HF and HCl from the gas flow. In a last stage, the autoclave is opened and drained, a sample of the organic phase is analyzed after having hydrolyzed and extracted the catalyst with a hydrochloric acid solution.

In the examples, one determines the rate of retention which makes it possible to determine if the reactants (and the heavies) do not accumulate in the reactor. Ideally, this rate of retention is null, which means that the level of the liquid phase remains constant. The higher this rate of retention is, the more the reaction is ineffective. It is pointed out that the rate of retention is defined as:

Rate retention=1−(mass of gas at the outlet)/(mass at the inlet)

Example 1

The starting reaction medium consists of an organic compound as a solvent, the 1,1,2-trichloro-2,2-difluoroethane, or F122 (152.7 g or 0.9 mole) and of a catalyst (0.197 moles of ethylmethylimidazolium chloride associated with 0.399 mole with $SbCl_5$, that is 0.197 moles of fluorinated complex catalyst emim⁻$Sb_2F_{11}$⁻), that is a molar ratio catalyst/F122 of 21.8 mol %. The temperature and the pressure are adjusted to the desired values which are indicated in the table. Chlorine is fed continuously with a flow of 0.7 g/h during the first hour of fluorination of catalyst then decreased to a flow of 0.1 g/h thanks to the special properties of the ionic liquid catalyst. The reactants HF and 1230xa are then introduced continuously. Table 1 describes the results obtained for various operating conditions tested according to the same mode of presentation as in table 1. The high percentage of 122 is due to the drive by the light ones.

TABLE 1

| Catalyst age | P | T | Flow HF | Flow 1230xa | RM | Rate of retention | Molar output 1233xf | Molar output 244bb | Analysis of the gaseous phase at the exit (% mol)* | | | | | |
|---|---|---|---|---|---|---|---|---|---|---|---|---|---|---|
| hr | bars | °C. | g/h | g/h | HF/1230xa | Wt % | (%) | (%) | 1230xa | 1233xf | 244** | 1232*** | C6F6H2Cl2 | 122 |
| 5 | 10 | 106 | 10.8 | 9.0 | 10.8 | 46.7 | 9.6 | 1.3 | 0.02 | 33.0 | 10.0 | 0.2 | 0 | 46.6 |
| 10 | 10 | 106 | 7.6 | 9.6 | 7.1 | 20.4 | 6.8 | 6.0 | 0.02 | 17.1 | 27.3 | 0.1 | 0 | 45.1 |
| 15 | 10 | 106 | 5.6 | 8.0 | 6.3 | 22.7 | 7.1 | 5.5 | 0.02 | 19.9 | 25.9 | 0.08 | 0 | 44.6 |
| 20 | 8 | 104 | 7.6 | 10.2 | 6.7 | 13.5 | 13.9 | 3.5 | 0.01 | 32.8 | 14.3 | 0.08 | 0 | 44.5 |
| 25 | 8 | 132 | 8.0 | 11.6 | 6.2 | 2.8 | 43.5 | 1.6 | 0.01 | 64.0 | 4.0 | 0.7 | 0 | 26.8 |
| 30 | 8 | 132 | 8.4 | 10.0 | 7.6 | 23.2 | 35.2 | 0.6 | 0.007 | 64.2 | 2.1 | 1.1 | 0 | 27.7 |
| 35 | 8 | 134 | 7.2 | 8.8 | 7.4 | 15.1 | 39.5 | 0.3 | 0.008 | 61.8 | 1.0 | 1.8 | 0 | 31.4 |
| 45 | 8 | 134 | 6.8 | 11.2 | 5.5 | 34.4 | 29.9 | 0.2 | 0.02 | 65.5 | 0.8 | 1.9 | 0 | 29.5 |

TABLE 1-continued

| Catalyst age | P | T | Flow HF | Flow 1230xa | RM | Rate of retention | Molar output 1233xf | Molar output 244bb | Analysis of the gaseous phase at the exit (% mol)* | | | | | |
|---|---|---|---|---|---|---|---|---|---|---|---|---|---|---|
| hr | bars | °C. | g/h | g/h | HF/1230xa | Wt % | (%) | (%) | 1230xa | 1233xf | 244** | 1232*** | C6F6H2Cl2 | 122 |
| 50 | 8 | 134 | 6.2 | 13.2 | 4.2 | 35.5 | 29.8 | 0.2 | 0 | 69.8 | 0.6 | 2.2 | 0 | 25.8 |
| 55 | 8 | 134 | 4.8 | 12.6 | 3.4 | 43.5 | 26.1 | 0.09 | 0 | 75.2 | 0.4 | 4.2 | 0 | 19.0 |
| 60 | 8 | 135.6 | 4.2 | 14.6 | 2.6 | 44.5 | 22.5 | 0.06 | 0 | 75.1 | 0.3 | 6.3 | 0.01 | 16.0 |
| 65 | 8 | 136 | 4.6 | 14.6 | 2.8 | 44.3 | 25.3 | 0.06 | 0 | 76.9 | 0.2 | 6.9 | 0.09 | 9.5 |

*other not identified products supplement the analysis
**assumption isomer 244bb
***assumption isomer 1232xf Following these tests, the reactor was drained. The organic phase contained 20% of unreacted 1230xa, the remainder being made of heavy compounds. The total material balance of the whole experimentation in weight is of 94%. The maximum molar output of 1233xf expressed in number of moles of 1233xf extracted from the reactor compared to the number of moles of 1230xa introduced over the same period is of 43%. These conditions in solvent medium are thus favorable.

Example 2

The starting reaction medium consists of an organics making it possible to be used as a solvent, the 1,1,2-trichloro-2,2-difluoroethane, or F122 (154.6 g or 0.91 mole) and of a catalyst (0.198 moles of ethylmethylimidazolium chloride associated with 0.404 mole with $SbCl_5$, either 0.198 moles of fluorinated complex catalyst emim$^-Sb_2F_{11}^-$), that is a molar ratio catalyst/F122 of 21.8 mol %. The temperature and the pressure are adjusted to the desired values which are indicated in the table. Chlorine is fed continuously with a flow of 0.7 g/h during the first hour of fluorination of catalyst then decreased to a flow of 0.1 g/h thanks to the special properties of ionic liquid catalyst. The reactants HF and 1230xa are then introduced continuously, as well as anhydrous hydrochloric acid. Table 4 described the results obtained for various operating conditions tested according to the same mode of presentation as in the previous examples. The same remark as for example 1 relative to the 122 applies here.

mum molar output in 1233xf expressed in number of moles of 1233xf extracted from the reactor compared to the number of moles of 1230xa introduced over the same period is of 73%. These conditions are favorable to the output in 1233xf. The rate of retention decreased and becomes in certain cases negative (the level of liquid decreases in the reaction zone). These conditions in solvent medium with a co-feed of anhydrous HCl are thus favorable.

The invention claimed is:

1. A process of fluorination of 1,1,2,3-tetrachloropropene comprising:
    (i) contacting 1,1,2,3-tetrachloropropene with hydrogen fluoride in a liquid phase in a solvent selected from the group consisting of 1,2-dichloroethane, 1,2,3-trichloropropane, 1-chloro-1-fluoroethane, 1,1-difluoroethane, 1,1-dichloroethane, 1,3-dichloro-1-fluorobutane, 1,1,1,3,3-pentafluorobutane, 1,1,2-trichloro-2,2-difluoroethane and mixtures thereof under conditions sufficient to form a reaction mixture comprising -HCl between 20 and 60%, HF between 10 and 40%, 2-chloro-3,3,3-trifluoropropene between 5 and 20%, 1,1,1,2-tetrafluoro-2-chloropropane between 0.5 and 5%, 2,3-dichloro-3,3-difluoropropene below 2% and solvent below 2%;
    (ii) separating the reaction mixture into a first stream comprising HCl, and a second stream comprising HF, 2-chloro-3,3,3-trifluoropropene and 1,1,1,2-tetrafluoro-2-chloropropane.

TABLE 2

| Catalyst age | P | T | Flow HF | Flow 1230xa | RM | Rate of retention | Molar output 1233xf | Molar output 244bb | Analysis of the gaseous phase at the exit (% mol)* | | | | | |
|---|---|---|---|---|---|---|---|---|---|---|---|---|---|---|
| hr | bars | °C. | g/h | g/h | HF/1230xa | Wt % | (%) | (%) | 1230xa | 1233xf | 244** | 1232*** | C6F6H2Cl2 | 122 |
| 5 | 8 | 133.2 | 6.2 | 9.6 | 5.8 | 18.7 | 25.5 | 6.6 | 0 | 48.7 | 12.6 | 0.1 | 0 | 32.0 |
| 10 | 8 | 132.2 | 4.8 | 9.6 | 4.5 | -2.9 | 50.1 | 4.7 | 0 | 60.8 | 5.7 | 0.1 | 0 | 27.9 |
| 15 | 8 | 132.1 | 6.4 | 11.0 | 5.2 | 9.2 | 61.3 | 1.2 | 0 | 75.8 | 1.4 | 0.4 | 0 | 19.2 |
| 20 | 8 | 132.1 | 6.2 | 10.2 | 5.5 | -16.4 | 72.6 | 0.8 | 0 | 67.4 | 0.7 | 0.4 | 0.009 | 27.3 |
| 25 | 8 | 132.5 | 10.6 | 18.0 | 5.3 | 13.0 | 45.6 | 0.2 | 0 | 63.2 | 0.3 | 1.4 | 0.13 | 30.8 |
| 30 | 8 | 133.6 | 12.0 | 22.4 | 4.8 | 16.4 | 34.2 | 0.1 | 0.02 | 56.9 | 0.1 | 3.4 | 1.8 | 32.1 |
| 35 | 8 | 133.6 | 5.4 | 10.2 | 4.8 | 13.0 | 42.1 | 0.1 | 0.09 | 66.2 | 0.2 | 2.8 | 4.5 | 20.3 |
| 45 | 8 | 143.1 | 5.4 | 8.8 | 5.5 | 3.6 | 53.9 | 0.1 | 0.05 | 72.5 | 0.1 | 4.3 | 7.2 | 10.0 |
| 50 | 8 | 135.4 | 6.2 | 11.0 | 5.1 | 15.3 | 33.4 | 0.1 | 0.14 | 67.8 | 0.2 | 3.2 | 16.8 | 3.4 |
| 55 | 8 | 145.1 | 5.8 | 10.0 | 5.2 | 10.8 | 37.1 | 0 | 0.37 | 67.5 | 0.1 | 7.1 | 15.3 | 1.0 |

*other not identified products supplement the analysis
**assumption isomer 244bb
***assumption isomer 1232xf Following these tests, the reactor was drained. The organic phase contained 18% of unreacted 1230xa, the remainder being made of heavy compounds. The total material balance of the whole experimentation in weight is of 94%. The maxi- 2. The process according to claim 1, in which the solvent is present in a quantity for a dilution ratio from at least 20%.

3. The process according to claim 1, in which a catalyst is used.

4. The process according to claim 3, in which the molar ratio catalyst/solvent is comprised between 10 mol % and 50 mol %.

5. The process according to claim 1 in which chlorine is added during the reaction.

6. The process according to claim 1, in which the product of the reaction is withdrawn in the gaseous state.

7. The process according to claim 1, wherein a gas is injected.

8. The process according to the claim 7, in which the flow of gas, compared to the flow of 1,1,2,3-tetrachloropropene, is such that the molar ratio of gas: 1,1,2,3-tetrachloropropene lies between 0.5:1 and 5:1.

9. The process according to claim 1, wherein step (ii) is a distillation step.

10. The process according to claim 1, wherein the second stream is further separated into a HF stream containing mainly HF, and an organic stream containing 2-chloro-3,3,3-trifluoropropene and 1,1,1,2-tetrafluoro-2-chloropropane.

11. The process according to claim 10, wherein the organic stream is further purified.

12. The process according to claim 11, wherein the organic stream is subjected to a further conversion process.

13. The process according to claim 1, further comprising a purging to withdraw heavies formed during step (i).

14. The process for preparing 2,3,3,3-tetrafluoropropene, comprising:
   (i) fluorinating of 1,1,2,3-tetrachloropropene into 2-chloro-3,3,3-trifluoropropene according to claim 1;
   (ii) converting 2-chloro-3,3,3-trifluoropropene into 2,3,3,3-tetrafluoropropene.

15. The process according to claim 14, in which the conversion of stage (ii) is a catalytic gas phase conversion.

* * * * *